(12) United States Patent
Hummel et al.

(10) Patent No.: US 7,217,544 B2
(45) Date of Patent: May 15, 2007

(54) METHOD FOR THE PREPARATION OF L-AMINO ACIDS FROM D-AMINO ACIDS

(75) Inventors: Werner Hummel, Titz (DE); Birgit Geueke, Zürich (CH); Steffen Osswald, Rodenbach (DE); Christoph Weckbecker, Gründau-Lieblos (DE); Klaus Huthmacher, Gelnhausen (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 11/056,165

(22) Filed: Feb. 14, 2005
(Under 37 CFR 1.47)

(65) Prior Publication Data
US 2006/0063238 A1    Mar. 23, 2006

(30) Foreign Application Priority Data
Feb. 19, 2004    (DE) .................. 10 2004 008 445

(51) Int. Cl.
| | |
|---|---|
| C12P 13/04 | (2006.01) |
| C12P 21/06 | (2006.01) |
| C12N 9/06 | (2006.01) |
| C12N 1/20 | (2006.01) |
| C12N 9/02 | (2006.01) |
| C07H 21/04 | (2006.01) |

(52) U.S. Cl. .............. 435/106; 435/191; 435/252.3; 435/189; 435/69.1; 536/23.2

(58) Field of Classification Search ........... 435/106, 435/191, 252.3, 189; 536/23.2
See application file for complete search history.

(56) References Cited

U.S. PATENT DOCUMENTS

| | | | |
|---|---|---|---|
| 5,854,035 A | 12/1998 | Stoyan et al. | 435/116 |
| 6,187,574 B1 | 2/2001 | Garcia Lopez et al. | 435/189 |
| 2003/0092033 A1* | 5/2003 | Weiner et al. | 435/6 |

FOREIGN PATENT DOCUMENTS

| | | |
|---|---|---|
| DE | 102 40 603 | 3/2004 |
| EP | 0 792 933 | 9/1997 |
| EP | 1 375 649 | 1/2004 |

OTHER PUBLICATIONS de Graaf, et al., "Metabolic Engineering for L-Lysine Production by Coryneformbacterium glutamicum," *Adv. Biochem. Eng. Biotechnol.* 73:9-29 (20001).

(Continued)

*Primary Examiner*—Tekchand Saidha
*Assistant Examiner*—Iqbal Chowdhury
(74) *Attorney, Agent, or Firm*—Michael A. Sanzo; Law Office of Michael A. Sanzo, LLC

(57) ABSTRACT

The invention relates to recombinant microorganisms which, in comparison to the starting organism, have a higher concentration or activity of a D-amino acid oxidase, of an L-amino acid dehydrogenase, of an NADH cosubstrate regenerating enzyme and, if necessary, of a catalase. The invention also includes methods for preparing L-amino acids from D-amino acids using of these microorganisms.

15 Claims, 3 Drawing Sheets

OTHER PUBLICATIONS

Enright, et al., "Stereoinversion of β- and γ-Substituted α-Amino Acids Using a Chemo-enzymatic Oxidation-Reduction Procedure," *Chem. Commun. 20*:2636-2637 (2003).

Gabler, et al., "Detection and Substrate Selectivity of New Microbial D-Amino Acid Oxidases," *Enzyme and Microbial Tech. 27*:605-611 (2000).

Galkin, et al., "Synthesis of Optically Active Amino Acids from α-Keto Acids with *Escherichia coli* Cells Expressing Heterologous Genes," *Appl. Environ. Microbiol. 63*(12):4651-4656 (1997).

Hanson, et al., "Enzymatic Synthesis of L-6-Hydroxynorleucine," *Biorg. Medicinal Chem. 7*:2247-2252 (1999).

Lin, et al., "Expression of *Trigonopsis variabilis* D-Amino Acid Oxidase Gene in *Escherichia coli* and Characterization of its Inactive Mutants," *Enzyme Microbiol. Technol. 27*:482-491 (2000).

Na'Amnieh, "Entwicklung eines rekombinanten Ganzzellsystems-Klonierung, Coexpression und Mutagenese der phenylalanin-Dehydrogenase aus *Rhodococcus* sp. M4 und des malic enzymes aus *E. coli* K12," Dissertation, 2002, Universitat Dusseldorf. English Language Abstract.

Nakajima, et al., "Enzymatic Conversion of Racemic Methionine to the L-Enantiomer," *J. Chem. Soc. Chem. Commun. 13*:947-948 (1990).

Patel, "Enzymatic Synthesis of Chiral Intermediates for Omapatrilat, and Antihypertensive Drug,"*Biomol. Eng. 17*:167-182 (2001).

Sahm, et al., "Construction of L-Lysine, L-Threonine-, or L-Isoleucine-Overproducing Strains of *Corynebacterium glutamicum*," *Ann. N.Y. Acad. Sci. 782*:25-39 (1996).

Schmid, et al., "The Use of Enzymes in the Chemical Industry in Europe," *Curr. Opin. Biotechnol. 13*(4):359-366 (2002).

Trost, et al., "Minimization of By-Product Formation During D-Amino Acid Oxidase Catalyzed Racemate Resolution of D/L-Amino Acids," *J. Mol. Cat. B: Enzymatic 19-20*:189-195 (2002).

English Language Abstract for Reference B1 (EP 0 792 933).

English Language Abstract for Reference B3 (DE 102 40 603).

\* cited by examiner

SEQUENCE LISTING

<160> NUMBER OF SEQ ID NOS: 12

<210> SEQ ID NO 1
<211> LENGTH: 33
<212> TYPE: DNA
<213> ORGANISM: Escherichia coli

<400> SEQUENCE: 1
ggaattccat atggatattc aaaaaagagt gag                33

<210> SEQ ID NO 2
<211> LENGTH: 33
<212> TYPE: DNA
<213> ORGANISM: Escherichia coli

<400> SEQUENCE: 2
gcgcgatatc tattagatgg aggtacggcg gta                33

<210> SEQ ID NO 3
<211> LENGTH: 29
<212> TYPE: DNA
<213> ORGANISM: Arthrobacter protophormiae

<400> SEQUENCE: 3
catgccatgg gtcccacagc accgttgag                    29

<210> SEQ ID NO 4
<211> LENGTH: 32
<212> TYPE: DNA
<213> ORGANISM: Arthrobacter protophormiae

<400> SEQUENCE: 4

-continued tttctgcagc tagctggccg gctcgccagc ca                                32

<210> SEQ ID NO 5
<211> LENGTH: 32
<212> TYPE: DNA
<213> ORGANISM: Bacillus cereus

<400> SEQUENCE: 5
catgccatgg gtacattaga atcttcgaa ta                                 32

<210> SEQ ID NO 6
<211> LENGTH: 30
<212> TYPE: DNA
<213> ORGANISM: Bacillus cereus

<400> SEQUENCE: 6
cggagctcta ttagcgacgg ctaataatat                                   30

<210> SEQ ID NO 7
<211> LENGTH: 30
<212> TYPE: DNA
<213> ORGANISM: Arthrobacter protophormiae

<400> SEQUENCE: 7
ggaattccat atgcccacag caccgttgag                                   30

<210> SEQ ID NO 8
<211> LENGTH: 69
<212> TYPE: DNA
<213> ORGANISM: Arthrobacter protophormiae

<400> SEQUENCE: 8
gaattccata tgtatatctc cttcttgcgg ccgcctgcag gatatcctag ctggccggct   60
cgccagcca                                                          69

<210> SEQ ID NO 9
<211> LENGTH: 64
<212> TYPE: DNA
<213> ORGANISM: Trigonopsis variabilis

<400> SEQUENCE: 9
ggaattccat atggctaaaa tcgttgttat tggtgccggt gttgccggtt taactacagc   60
tctt                                                               64

<210> SEQ ID NO 10
<211> LENGTH: 38
<212> TYPE: DNA
<213> ORGANISM: Trigonopsis variabilis

<400> SEQUENCE: 10
cgggatccct aaaggtttgg acgagtaaga gctctttc                          38

<210> SEQ ID NO 11
<211> LENGTH: 31
<212> TYPE: DNA
<213> ORGANISM: Escherichia coli

<400> SEQUENCE: 11
cggagctcat gacattagaa atcttcgaat a                                 31

<210> SEQ ID NO 12
<211> LENGTH: 30

```
-continued

<212> TYPE: DNA
<213> ORGANISM: Escherichia coli

<400> SEQUENCE: 12
cggagctcta ttagcgacgg ctaataatat                                              30
```

METHOD FOR THE PREPARATION OF L-AMINO ACIDS FROM D-AMINO ACIDS

CROSS REFERENCE TO RELATED APPLICATIONS

The present application claims priority to German application 10 2004 008 445.9, filed on Feb. 19, 2004, the contents of which is hereby incorporated by reference.

FIELD OF THE INVENTION

The present invention relates to recombinant microorganisms which, in comparison to the starting organisms, have a higher concentration or activity of: a) a D-amino acid oxidase; b) an L-amino acid dehydrogenase; and c) an NADH cosubstrate-regenerating enzyme. In addition, the recombinant microorganism may include a higher concentration or activity of a catalase. The invention is also directed to methods in which these microorganisms are used in the preparation of L-amino acids from D-amino acids.

BACKGROUND OF THE INVENTION

Many natural amino acids are prepared in enantiomerically pure form by fermentation using genetically modified bacteria (de Graaf, et al., *Adv. Biochem. Eng. Biotechnol.* 73:9–29 (2001); Sahm, et al., *Ann. NY Acad. Sci.* 782:25–39 (1996)). Although not all proteinogenic amino acids (and only very few unnatural or D-amino acids) can be prepared in this way, chemical syntheses for enantiomerically pure amino acids are very costly. As a result, several enzymatic processes have been developed, and used on a scale of several metric tons per year. The methods range from kinetic racemate cleavage with the aid of acylases, amidases, esterases, hydantoinases, amino acid oxidases and proteases, to enantioselective syntheses by means of lyases, aminotransferases and dehydrogenases (Schmid, et al., *Curr. Opin. Biotechnol.* 13(4):359–366 (2002)).

In addition to enantioselective syntheses, enantiomerically enriched amino acid preparations may be obtained by dynamic kinetic racemate cleavages, in which the unwanted enantiomer is racemized in situ. A 100% yield can be achieved by combining a D- or L-amino acid oxidase with an unselective chemical reduction of the incipient imino acid back to the principal amino acid. The reducing agent, e.g., NaBH$_4$, must, however, be employed in an excess of at least 25 equivalents, which makes this option very costly (Enright et al., *Chemical Communications* 20:2636–2637 (2003)).

The amination of α-ketonic acids by amino acid dehydrogenases is generally known. Although the educt is many times more costly than, for example, the corresponding racemic amino acid, by coupling an amino acid oxidase with an amino acid dehydrogenase the corresponding ketonic acid can be obtained in situ from an amino acid. When both of the enzymes have the opposite enantio-selectivity, a D-amino acid can be completely converted into an L-amino acid or an L-amino acid converted into a D-amino acid. Thus, starting with a racemate, an enantiomerically pure compound can be produced. In order to make the process economically viable, the NADH cosubstrate must be enzymatically regenerated. Enzymes such as formate dehydrogenase and malate dehydrogenase (decarboxylating) which liberate carbon dioxide from its substrate and thus make the reaction irreversible, are particularly well suited for this (Hanson, et al., *Bioorganic Medicinal Chem.* 7(10):2247–2252 (1999); Nakajima, et al., *J. Chem. Soc. Chem. Commun.* 13:947–8 (1990)).

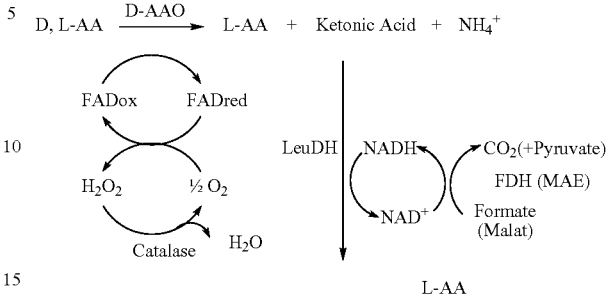

For a rapid and complete conversion in the cell-free system, a catalase must also be present. This is needed because hydrogen peroxide is produced in the oxidative step catalyzed by the amino acid oxidase and this leads to the decarboxylation of the ketonic acid and to deactivation of enzymes (Trost, et al, *J. Mol. Catalysis B: Enzymatic* 19–20:189–195 (2002)). The conversion of racemate into enantiomerically pure amino acids is possible in this system with >99% ee and >95% yield. However, this method is costly, since four different enzymes have to be separately prepared and isolated.

SUMMARY OF THE INVENTION

In its first aspect, the invention is directed to a recombinant microorganism, which has been engineered in such a way that, compared to the starting organism, it has a higher concentration or activity of: a) a D-amino acid oxidase; b) an L-amino acid dehydrogenase; and c) an enzyme that regenerates NADH. The "starting organism" is the microorganism prior to the performance of steps to increase activity, e.g., prior to transformation with a vector encoding an enzyme. The recombinant microorganism may be made by transforming the starting microorganism with one or more vectors, that together encode: a D-amino acid oxidase; an L-amino acid dehydrogenase; and an enzyme that regenerates NADH. Thus, after transformation has been completed, the recombinant microorganism has at least one additional copy of: a polynucleotide; encoding a D-amino acid oxidase; a polynucleotide encoding an L-amino acid dehydrogenase; and a polynucleotide encoding an enzyme that regenerates NADH.

Preferred D-amino acid oxidases include: the D-amino acid oxidase of *arthrobacter protophormiae* (accession number gi2140775); the D-amino acid oxidase of *trigonopsis variabilis* (accession number gi1616634); the D-aspartate oxidase of *bos taurus* (accession number gi27806895); the D-amino acid oxidase of *rhodosporidium*; and the D-amino acid oxidase of *rhototorula gracillis*. Preferred L-amino acid dehydrogenases include: the L-leucine dehydrogenase of *bacillus cereus* (accession number gi6741938); the L-phenylalaninedehydrogenase of *rhodococcus* (accession number gi625925); the L-lysine dehydrogenase of *homo sapiens*; the L-alanine dehydrogenase of *bacillus subtilis* (accession number gi6080244); and the glutamate dehydrogenase of *bos Taurus* (accession number gi118533). Preferred enzymes regenerating NADH include: a formate dehydrogenase; a malate dehydrogenase; and an alcohol dehydrogenase, each from *arthrobacterprotophormiae, trigonopsis variabilis* or *E. coli*. Optionally, microorganisms may also be transformed with a vector that increases the intracellular concentration or activity of a catalase. Preferred microorganisms include cells of the *staphylococcus streptomyces*; and *Escherichia* genus, with the most preferred species being *E. coli*

In another aspect, the invention includes the vectors used to produce the recombinant microorganisms described above. These will typically be expression vectors in which there is a coding sequence corresponding to an enzyme that is linked to a promoter. The vector should encode at least two of the enzymes needed to make cells that convert D-amino acids to L-amino acids. Thus, a vector may encode: a) a D-amino acid oxidase and an L-amino acid dehydrogenase; b) a D-amino acid oxidase and an enzyme that regenerates NADH; c) a D-amino acid oxidase and a catalase; d) an L-amino acid and an enzyme that regenerates NADH; e) an L amino acid and a catalase; and f) an enzyme that regenerates NADH and a catalase The invention also encompasses methods for manufacturing an L-amino acids from a D-amino acid by reacting the recombinant microorganisms described above with the D-amino acid under conditions in which the relevant enzymes are all active and then isolating the L-amino acid. The preferred enzymes and organisms are the same as those described above. In order to make cells permeable, it will generally be useful to treat the cells with chemicals. Preferred D amino acids for use in the invention include: lysine, arginine, phenylalanine, valine, ornithine, leucine, histidine, norleucine, tyrosine, alanine, glutamate, cephalosporine, and methionine.

BRIEF DESCRIPTION OF THE DRAWINGS

FIG. 1 shows plasmids which carry the genes needed in the conversion process in different combinations: malic enzyme (MAE), leucine-dehydrogenase (LeuDH), D-AAO from *arthrobacter protophormiae* (ApD-AAO) and D-AAO from *trigonopsis variabilis* (TvD-AAO). Example 1 provides additional information on the construction of plasmids.

DESCRIPTION OF THE INVENTION

Figure 1:
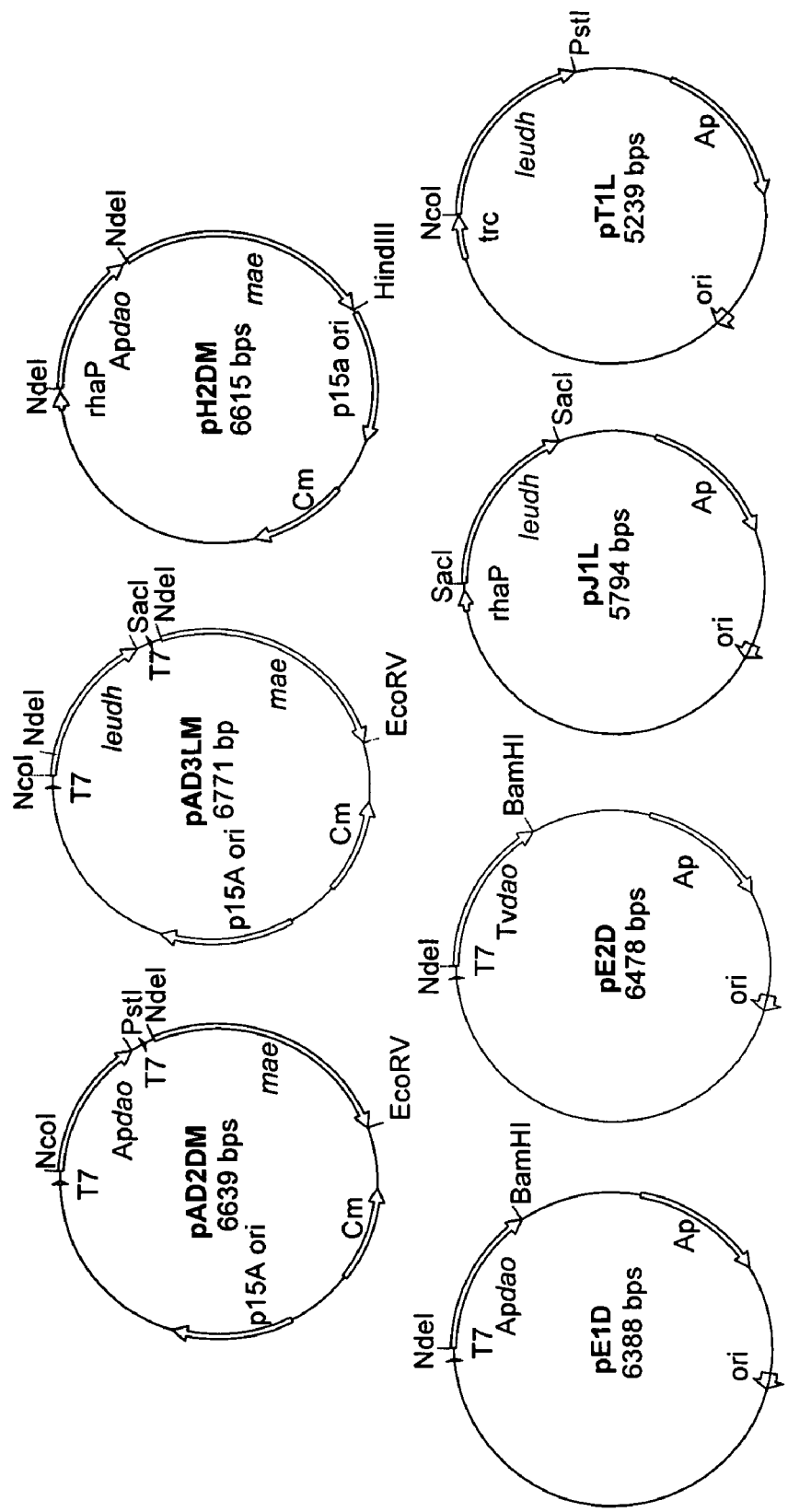
FIG. 1: Plasmids Carrying Genes Needed in the Conversion of D-Amino Acids to L-Amino Acids.

The present invention is directed to a method that avoids the costly isolation and preparation of the enzymes needed for the conversion of D-amino acids into L-amino acids. The method preferably utilizes static cells of a recombinant microorganism which, in comparison to the starting organism, e.g., the wild type, has a higher concentration or activity of a D-amino acid oxidase, an amino acid dehydrogenase, an NADH co-substrate regenerating enzyme and, if necessary, a catalase. Oxidases and dehydrogenases are combined with regard to the substrate that is to be converted and the substrate spectrum of the enzymes. The starting organism, i.e., the organism prior to recombinant transformation, does not have to contain the enzymes.

Formate hydrogenases, malate dehydrogenases (German Patent 102 40 603) or alcohol dehydrogenases can be employed as regenerating enzymes for the NADH co-substrate. The source of the polynucleotides encoding these enzymes is, in general, not limited to the strain or species of the starting microorganism. The origin of the genes can be microorganisms, molds or yeasts, especially *Arthrobacter protophormiae* or *trigonopsis variabilis* for D-AAO, and *bacillus cereus* for LeuDH. Microorganisms that are preferred as host organisms are those for which there are stable expression systems, such as *Bacillus*, various molds, *staphylococcus* or *streptomyces*, and especially *E. coli*.

Preferred amino acid dehydrogenases include: L-leucin dehydrogenase from *bacillus* species (EP 792 933); glutamate dehydrogenase; L-phenylalanine dehydrogenase from *rhodococcus* species; and L-alanine dehydrogenase from *thermoactinomyces* or *bacillus* strains. The particular enzyme selected will be determined by the ketonic acid that is to be reductively aminated.

D-amino acid oxidases or polynucleotides encoding these enzymes may be obtained from: the *rhototorula gracillis* yeast (U.S. Pat. No. 6,187,574); *trigonopsis variabilis* (Lin, et al., *Enzyme Microbial Technol.* 27:482–491 (2000)); *Candida* species; the *neurospora crassa* molds; *verlicullium luteoralbo* and different *fusarium* species; and *arthrobacter protophormiae* (European Patent 1 375 649). An overview of the substrates of different D-AAOs can be found in Gabler, et al. (*Enzyme Microbiol. Technol.* 27(8):605–611 (2000)). The D-AAO from *rhodosporidium* and corresponding gene is described in European Patent 897 006 A1. As with the amino acid dehydrogenase, the particular D-amino acid oxidase selected will be determined by the substrate that is to be converted and the host strain that will used. Thus, for example, for the de-racemization of DL-methionine or DL-leucine, preferably the D-amino acid oxidase from arthrobacter protophormiae (European Patent 1 375 649A) and leucin dehydrogenase from *bacillus cereus* coding genes are over-expressed in *E. coli*. The tables below contain exemplary genes and encoded enzymes that can be employed in accordance with the invention:

TABLE 1

D-Amino acid Oxidases

| Accession No. or reference | organism | enzyme |
|---|---|---|
| gi2140775 | *arthrobacter protophormiae* | D-amino acid oxidase |
| gi1616634 | *trigonopsis variabilis* | D-amino acid oxidase |
| gi27806895 | *bos taurus* | D-aspartate oxidase |
| EP 897 006 | *rhodosporidium* | D-amino acid oxidase |
| U.S. Pat. No. 6,187,574 | *rhototorula gracillis* | D-amino acid oxidase |

TABLE 2

L-Aminoacid Dehydrogenases

| Accession No. | Organism | Enzyme |
| --- | --- | --- |
| gi6741938 | bacillus cereus | L-leucin dehydrogenase |
| gi625925 | rhodococcus spec. | L-phenylalaninedehydrogenase |
| — | homo sapiens | L-lysine dehydrogenase |
| gi16080244 | bacillus subtilis | L-alanine dehydrogenase |
| gi118533 | bos Taurus | glutamate dehydrogenase |

The DNA sequences obtained can be analyzed by means of known algorithms or sequence-analysis programs such as, for example, that by Staden (*Nucl. Ac. Res.* 14:217–232 (1986)), that by Marck (*Nucl. Ac. Res.* 16:1829–1836 (1988)) or the GCG Program by Butler (*Meth. Biochem. Anal.* 39:74–97 (1998). A person skilled in the art will find guidelines for the amplification of DNA sequences using the Polymerase Chain Reaction (PCR), inter alia, in the handbook by Gait (*Oligonucleotide Synthesis: A Practical Approach*, (IRL Press, Oxford, UK, 1984)) and in Newton, et al. (*PCR* (*Spektrum Akademischer Verlag*, Heidelberg, Germany (1994)).

Another object of the invention is to provide host strains containing autonomously replicating vectors that are, in general, compatible with each other and that encode at least one gene (and preferably all three genes) that codes for an enzyme in accordance with the invention as described above. DNA vectors can be introduced into eukaryotic or prokaryotic cells using transformation techniques well known in the art. Preferably the vectors used to transform cells encode nucleotide sequences for two enzymes, especially, the combination of either malate dehydrogenase and an amino acid dehydrogenase or malate dehydrogenase and a D-amino acid oxidase. Another preferred vector encodes the combination of an amino acid dehydrogenase and a D-amino acid oxidase. In each case, the nucleotide sequence for the third enzyme needed in the above described process is supplied by another vector. For example, a cell might be transformed with one vector designed for the expression of malate dehydrogenase and an amino acid dehydrogenase and a separate vector for a D-amino acid oxidase.

Genes with good expressability may be cloned using a vector with a low number of copies, and genes with weaker expression capability using a vector with a higher number of copies and/or strong promoter. Host cells are transformed with these vectors in such a way that, in comparison to the starting organism, at least an additional copy of a gene needed for carrying out the conversion of D- to L-amino acids is present at the end of the transformation. Ultimately, polynucleotide sequences encoding at least three and, typically four, enzymes will need to be overexpressed and there will generally be at least one additional copy of a sequence for each of these present and expressed in a host cell. However, other methods of overexpressing gene that are known in the art may also be used. For example, homologous recombination may be used to alter the promoter, regulation region or ribosome binding location of an endogenous gene, i.e., the gene normally found in the cellular genome. Expression cassettes which are formed upstream of the structural gene work in a similar way.

Other strategies for increasing expression may also be used either alone or in conjunction with the techniques described above. For example, inducible promoters, may be used to increase expression at specific times in the course of fermentative amino acid production. Alternatively, measures known in the art may be used to extend the lifetime of mRNA or to slow the rate at which enzymes are broken down. Although genes or gene constructs may be maintained in cells on plasmids, they may also be integrated into the cellular genome and amplified in chromosomes. Nonrecombinant techniques can also be used to increase expression. For example, over-expression can be aided by altering the composition of the medium used to culture cells and the conditions present during the fermentative production of amino acids.

Guidance with respect to techniques for overexpressing genes may be found in many references including: Martin, et al., *Bio/Technology* 5:137–146 (1987); Guerrero, et al., *Gene* 138;35–41 (1994); Tsuchiya, et al., *Bio/Technology* 6:428–430 (1988)); Eikmanns, et al., *Gene* 102:93–98 (1991); European patent 472 869; U.S. Pat. No. 4,601,893; Schwarzer, et al., *Bio/technology* 9:84–87 (1991); Reinscheid, et al., *Appl. Environ. Microbiol.* 60:126–132 (1994); LaBarre, et al., *J. Bacteriol.* 175:1001–1007 (1993); international patent application WO 96/15246; Malumbres, et al., *Gene* 134:15–24 (1993); unexamined Japanese application JP-A-10-229891; Jensen, et al., *Biotech. Bioeng.* 58:191–195 (1998); Makrides, *Microbiol. Rev.* 60:512–538 (1996); and in textbooks of genetics and molecular biology. Over-expression leads to an increase in the intracellular activity or concentration of the corresponding enzyme. The increase is, in general, at least 10 to 500% or 100 to 500% up to a maximum of 1000 or 2000% of the concentration or activity of the enzyme prior to overexpression, i.e., in the starting organism.

The invention also encompasses a method for the preparation of L-amino acids from D-amino acids characterized by the use of a recombinant microorganism which, in comparison with the starting organism, has a higher concentration or activity of a D-amino acid oxidase, an L-amino acid dehydrogenase, an NADH cosubstrate regenerating enzyme and, if necessary, a catalase. The recombinantly engineered organism is exposed to a solution containing D-amino acid(s) and the resulting L-amino acid is isolated. Malic enzyme is preferably used as the cosubstrate regenerating enzyme. When this is the case, the buffered aqueous solution containing the whole-cell catalyst and the D-amino acid that is to be converted should also contain L-malate or L-malic acid in a ratio at least equimolar to, and preferably 1.5 to 6 times the molar quantity of the D-amino acid.

If necessary a catalase is also overexpressed as a peroxide decomposing enzyme. Catalases from many different organisms should be suitable, including, for example, the enzyme from *Escherichia coli* (catalase HPII (hydroxyperoxidase II) Accession number: gi115722).

The conversion of the D-amino acid is preferably carried out with static cells. These are cells that are viable, but not actively multiplying. Amino acids produced in this connection include naturally occurring as well as synthetic α-amino acids as described, for example, in Beyer-Walter (*Textbook of Organic Chemistry* (Lehrbuch der organischen Chemie), S. Hirzel Publishers, Stuttgart, $22^{nd}$ edition, 1991, p. 822 et seq.). Mixtures of D and L amino acids, their racemates or pure D-enantiomers may be used. Preferred amino acids are selected from the group: lysine, arginine, phenylalanine, valine, ornithine, leucine, histidine, norleucine, tyrosine, alanine, glutamate, and cephalosporine. The most preferred amino acid is methionine.

Certain enzymes are especially well suited for the conversion of the different D-amino acids (see Gabler et al., *Enzyme Microbiol. Technol.* 27(8):605–611 (2000)). For example, the D-AAO from arthrobacter protophormiae is especially suitable for the conversion of basic and hydrophobic amino acids. Suitable enzymes and nucleotide sequences may be selected based upon information known in the art.

One advantage of the process described herein is that the isolation of individual enzymes is avoided. A second advantage is that the cells employed in accordance with the invention (total cell catalyst) can be easily separated after the reaction. In the conversion of D-methionine to L-methionine using isolated enzymes, catalase must be added (Nakajima, et al., *J. Chem. Soc. Chem. Commun.* 13:947–8 (1990)) whereas this may not always be absolutely necessary using whole cell catalysts.

The microorganisms that have been engineered for use in the process described as above are also part of the invention and can be cultivated continuously or discontinuously in a batch (batch cultivation), fed batch, or repeated fed batch process. A summary of cultivation methods is provided in the textbook by Chmiel (*Bioprocess Technology 1. Introduction to Bioprocess Technology* (Biofahrensstechnik 1. Einführung in die Biofahrenstechnik), Gustav Fischer publishers, Stuttgart (1991)) or in the textbook by Storhas (*Bioreactors and Peripheral Equipment* (Bioreaktoren und periphere Einrichtungen (Vieweg Publishers, Braunschweig/Wiesbaden, (1994)).

The culture medium used must satisfy the needs of the cells. Descriptions of culture media for different microorganisms may be found in the Handbook "Manual of Methods for General Bacteriology" of the American Society for Bacteriology (Washington D.C., USA 1981). The medium may include, as sources of carbon: sugar and carbohydrates such as glucose, saccharose, lactose, fructose, maltose, molasses, starch and cellulose; oils and fats such as soy oil, sunflower oil, groundnut oil and coconut oil; fatty acids such as palmitic acid, stearic acid and linoleic acid; alcohols such as glycerine and ethanol; and organic acids such as acetic acid. These materials can be used singly or as a mixture.

As a nitrogen source, the medium may include organic nitrogen-containing compounds such as peptone, yeast extract, meat extract, malt extract, cornsteep liquor, soybean flour and urea or inorganic compounds such as ammonium sulfate, ammonium chloride, ammonium phosphate, ammonium carbonate and ammonium nitrate. As a source of phosphorus, the medium may include: phosphoric acid, potassium hydrogen phosphate, dipotassium hydrogen phosphate or the corresponding sodium salts. The culture medium must also contain metal salts such as magnesium sulfate or iron sulfate, which are necessary for growth. Finally, the medium must include essential growth hormones such as amino acids and vitamins. These materials can be added to the culture in the form of a one-time additive or be fed in during the process of culturing.

For pH control of the culture, basic compounds such as sodium hydroxide, potassium hydroxide, ammonia or ammonia water, or acid compounds such as phosphoric acid or sulfuric acid may be added. Cultures may include antifoaming agents, such as fatty acid polyglycolesters, and agents to maintain plasmid stability, such as antibiotics. To maintain aerobic conditions, oxygen or oxygen-containing gas mixtures such as air can be introduced into the medium. The culture temperature should normally be between 20° C. and 45° C. and preferably from 25° C. to 40° C.

Culturing should be continued until the logarithmic growth phase of cells has been passed. This goal is normally attained in from 10 to 20 hours. Subsequently, the cells are preferably harvested, washed and introduced into a buffer as a suspension at a pH of 6–9, and preferably 6.8 to 7.9. The cell concentration should be 1–6%, and preferably 1.5 to 4% (moist weight). The cells should then generally be permeabilized using physical or chemical methods, for example with toluene as described in Wilms, et al. (*J. Biotechnol.*, 86:19–30 (2001)). This should allow the D-amino acid to be metabolized to readily penetrate the cell wall and leak out after conversion. After being permeabilized, the cell suspension is mixed with a D-amino acid and L-malate or L-malic acid containing solution. Conversion takes place at 10 to 40° C., especially 25 to 36° C., at a pH of between 6.8 and 8.9, and preferably between 7.5 and 8.5. The process is stopped by heating cells to 70 to 100° C.

EXAMPLES

Example 1

Construction of Plasmids

A series of plasmids is constructed which carry the genes needed in the conversion process in different combinations: malic enzyme (MAE), leucine-dehydrogenase (LeuDH), D-AAO from *arthrobacter protophormiae* (ApD-AAO) and D-AAO from *trigonopsis variabilis* (TvD-AAO). Construction takes place using the primers and plasmids listed in table 3.

For amplification of the genes of ApD-AAO (Apdao; gi32140775), of TvD-AAO (TVdao; gi1616634) and of malic enzymes (mae; gi1787752) genomic DNA from *arthrobacterprotophormiae, trigonopsis variabilis* and *E. coli* K12 is used as templates. The gene encoding leucine dehydrogenase (leudh; gi:6741938) was amplified with the plasmid pT1L (=pLeuB), (Ansorge, et al, *Appl. Microbiol. Biotechnol.* 53:668–73 (2000)). Using the primers listed in table 3, restriction cut locations were inserted by means of PCR. With the forward primer DAAOTvforNdeI, the intron was removed into the Tvdao gene. In the cloning of Apdao gene in pH1M a Shine-Dalgamo sequence and additional restriction cut locations (for EcoRV, PstI and NotI) were incorporated by PCR, while the reverse primer ApNdeIrev (table 1) was used.

TABLE 3

Plasmids and Primers

| Name | Plasmid/Gene | Primer |
|---|---|---|
| pE1D | pET21a/Apdao | European Patent 1375 649 A |
| pHWG640 | pACYC-Derivativ/mae | Altenbucher, et al., Curr. Opin. Biotechnol. 12(6): 559–563 (2001) |

TABLE 3-continued

Plasmids and Primers

| Name | Plasmid/Gene | | Primer |
|---|---|---|---|
| pT1L (=pLeuB) | pTrc99a/leudh | | Ansorge, et al., Appl. Microbiol. Biotechnol. 53(6): 668–673 (2000) |
| pAD1M | pACYC-Duet/ mae | MEfNdeI | 5' ggaattccatatggatattcaaaaaagagtgag 3' (SEQ ID NO: 1) |
| | | MErEcoRV | 5' gcgcgatatctattagatggaggtacggcggta 3' (SEQ ID NO: 2) |
| pAD2DM | pAD1M/Apdao | ApNcoIfor_2 | 5' catgccatgggtcccacagcaccgttgag 3' (SEQ ID NO: 3) |
| | | ApPstIrev | 5' tttctgcagctagctggccggctcgccagcca 3' (SEQ ID NO: 4) |
| pAD3LM | pAD1M/leudh | LeuDHfNcoI_2 | 5' catgccatgggtacattagaaatcttcgaata 3' (SEQ ID NO: 5) |
| | | LeuDHrSacI | 5' cggagctctattagcgacggctaataatat 3' (SEQ ID NO: 6) |
| pH1DM | pHWG640/Apdao | ApNdeIfor_2 | 5' ggaattccatatgcccacagcaccgttgag 3' (SEQ ID NO: 7) |
| | | ApNdeIrev | 5' gaattccatatgtatatctccttcttgcggccgcctgca ggatatcctagctggccggctcgccagcca 3' (SEQ ID NO: 8) |
| pE2D | pET21a/Tvdao | DAAOTvforNdeI | 5' ggaattccatatggctaaaatcgttgttattggtgccgg tgttgccggttttaactacagctctt 3' (SEQ ID NO: 9) |
| | | DAAOTvrevBamHI | 5' cgggatccctaaaggtttggacgagtaagagctctttc 3' (SEQ ID NO: 10) |
| pJ1L | pJOE4036/leudh | LeuDHfSacI | 5' cggagctcatgacattagaaatcttcgaata 3' (SEQ ID NO: 11) |
| | | LeuDHrSacI | 5' cggagctctattagcgacggctaataatat 3' (SEQ ID NO: 12) |

Example 2

Construction of Expression Strains

Using a suitable combination of plasmids, the recombinant *E. coli* strains listed in table 4 were constructed. In each case, the strain contains a gene for an amino acid oxidase, a leucine dehydrogenase and a malic enzyme. Starting strains were BL21 (DE3) from Novagen and JM109 from Stratagene.

TABLE 4

*E. Coli* Strains

| No. | E. coli Strain | Plasmid 1 | Plasmid 2 | Inductor | Resistance |
|---|---|---|---|---|---|
| 1 | BL21(DE3) | pAD3LM | pE1D | IPTG | $Ap^R$, $Cm^R$ |
| 2 | BL21(DE3) | pAD3LM | pE2D | IPTG | $Ap^R$, $Cm^R$ |
| 3 | BL21(DE3) | pAD2DM | pJ1L | ITPG + Rha | $Ap^R$, $Cm^R$ |
| 4 | BL21(DE3) | pAD2DM | pT1L | IPTG | $Ap^R$, $Cm^R$ |
| 5 | JM109 | pH2DM | pJ1L | Rha | $Ap^R$, $Cm^R$ |
| 6 | BL21(DE3) | pH2DM | pJ1L | Rha | $Ap^R$, $Cm^R$ |
| 7 | JM109 | pH2DM | pT1L | IPTG + Rha | $Ap^R$, $Cm^R$ |
| 8 | BL21(DE3) | pH2DM | pT1L | IPTG + Rha | $Ap^R$, $Cm^R$ |

The strain designation (1–8) is retained in the following examples of the corresponding table.

Example 3

Verification of Intracellular Enzyme Activities

Figure 2:
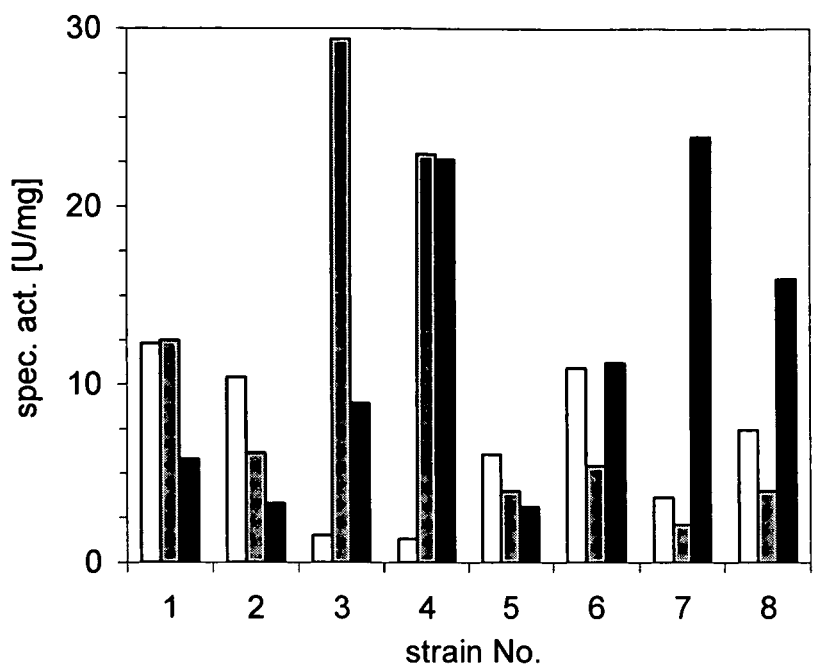
FIG. 2: Biotransformation Reaction with Recombinant Strains (Whole Cell Catalyst). *E. coli* strains engineered to overexpress enzymes needed in the conversion of D-amino acids to L-amino acids are cultured under aerobic conditions and the activity of the various enzymes is measured. Results are shown in FIG. 2 with: white=D-AAO; grey=MAE; and black=LeuDH. Additional information on assays may be found in Example 3.

The strains shown in table 4 are cultured under standard conditions in Luria-Bertani (LB) medium at pH 7.5. Depending on the plasmid transformed, 100 μg ml$^{-1}$ of ampicillin and/or 34 μg ml$^{-1}$ of chloramphenicol are added to the medium. For enzyme expression, the recombinant *E. coli* strains were cultured under aerobic conditions in a 100 ml vibrating flask together with 20 ml of the medium. The cells were incubated at 37° C. at 200 rpm in a vibratory rotating machine and induced at an OD550 of about 0.5 with 100 μM IPTG and/or 0.2% rhamnose. Following this induction the strains were further incubated at 30° C. The enzyme activity measured is presented in FIG. 2 with: white=D-AAO; grey=MAE; and black=LeuDH. Strain 6 shows the effectiveness of the rhamnose promoter.

Example 4

Biotransformation Reactions with Whole Recombinant Strains (A) D,L-methionine

As an example of a deracemization, the racemate of methionine is utilized as the substrate and converted by whole recombinant *E. coli* cell strain 1 (corresponding to table (2)), which contains both of the pAD3LM plasmids (carrying genes for leucine dehydrogenase and malic enzyme) and pE1D (carrying the gene for the *arthrobacter protophormiae* D-amino acid oxidase).

HPLC can be used to follow the catalyzed synthesis of L-met through the oxidase catalyzed breakdown of D-met and reductive amination. The reaction solution contains: 25 mM D,L-met, 100 mM L-malate, 0.7 M $NH_4Cl$, 50 mM tris, and 10 mM $MgCl_2$, at a final pH of 8.0, The cells are suspended in 50 mM TEA/HCl pH 7.6 buffer, and mixed with 10 μl/ml of toluene, this suspension is stirred for 30 min at 30° C. and then set up for the reaction. The cell concentration in the reaction amounts to 3.3% (moist weight per unit volume) in a final volume of 1 ml. The conversion takes place at 1000 rpm with shaking in a Thermomixer 5436 (Eppendorf company). Conversion is stopped by heating for 5 min at 95° C. and the clear excess is analyzed by HPLC.

Figure 3:
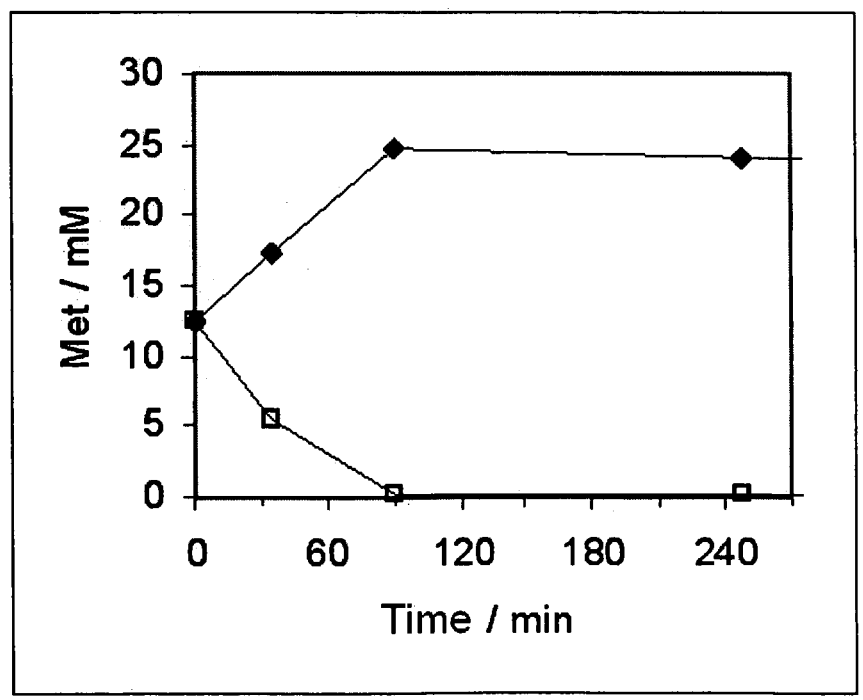
FIG. 3: Conversion of D-Met to L-Met Using Whole Cell Catalyst: An *E. coli* strain transformed to overexpress leucine dehydrogenase, malate dehydogenase and *Arthrobacter Protophormiae* D-amino acid oxidase is assayed for its ability to convert D-methionine methionine (open squares) to L-methionine (darkened squares). Further information on assays can be found in Example 4.

The samples are derivatized to determine the concentration of D- and L-met, after dilution. Specifically, 20 μl of a solution of 260 mM isobutyric-L-cysteine and 170 mM o-phthalic dialdehyde in 100 mM sodium borate buffer at pH 10.4 were added to preparations. HPLC separation conditions are available as published (Krieg, et al., *Adv. Synth. Catal.*, 344 (9):965–73 (2002)). The breakdown of D-met and the formation of L-met are summarized in FIG. 3. An enantiomerically pure L-met product is obtained having a final concentration of 25 mM.

(B) D-leucine

Figure 4:
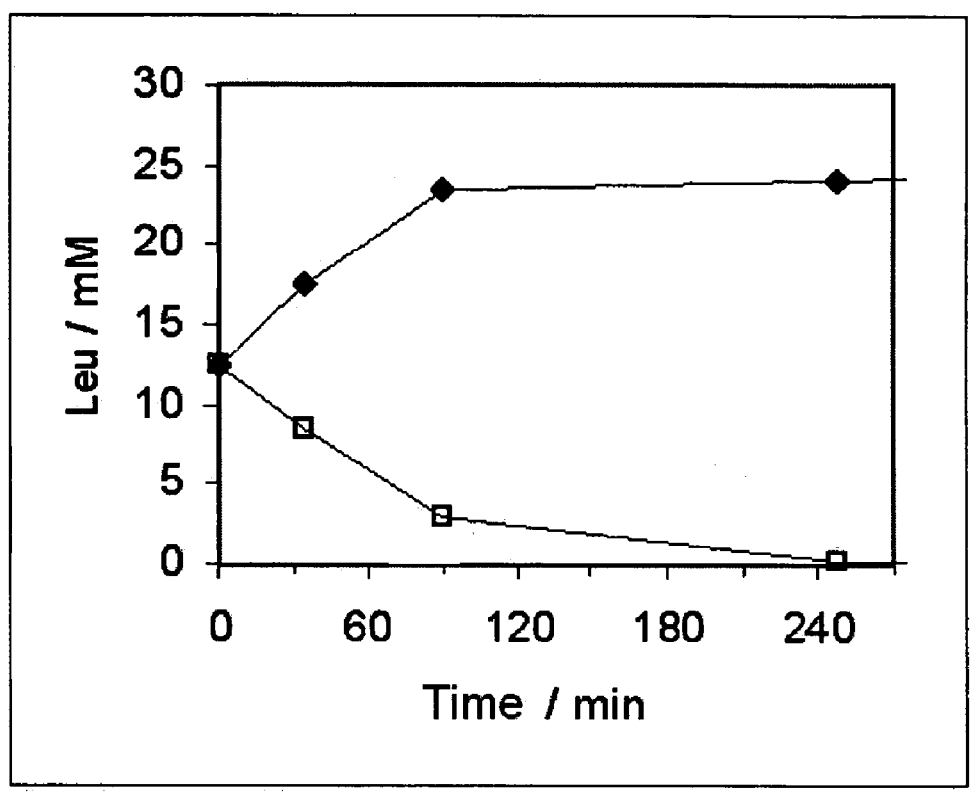
FIG. 4: Conversion of D-Leu to L-Leu Using Whole Cell Catalyst: Assays were performed to determine the ability of the recombinant *E. coli* strain to convert D-leucine to L-leucine and results are shown in the figure. Open squares correspond to D-leu concentration and darkened squares correspond to L-leu concentration. Further information on the assay may be found in Example 4.

In manner analogous to that described in part A, a solution of 25 mM D,L-leucine is reacted. Details of the reaction itself and the HPLC analysis are as described above. The breakdown of D-leu and the formation of L-leu are shown together in FIG. 4. An enantiomerically pure product of L-leu is obtained having a final concentration of 25 mM.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method for manufacturing an L-amino acid from a D-amino acid comprising:
   a) reacting a recombinant microorganism with said D-amino acid, wherein:
      i) said recombinant microorganism has been made by transforming a starting microorganism with one or more vectors comprising polynucleotides encoding the enzymes: D-amino acid oxidase, wherein said D-amino acid oxidase is the D-amino acid oxidase of *A. protophormiae;* L-amino acid dehydrogenase, wherein said L-amino acid dehydrogenase is the L-amino acid dehydrogenase of *Bacillus cereus;* and an enzyme that regenerates NADH, wherein said enzyme that regenerates NADH is the malate dehydrogenase from *A. protophormiae;*
      ii) relative to said starting microorganism, said recombinant microorganism overexpresses each of said enzymes;
      iii) the reaction is carried out under conditions in which each of said enzymes is active; and
   b) isolating said L-amino acid.

2. The method of claim 1, wherein relative to said starting microorganism, said recombinant microorganism has at least one additional copy of:
   a) a polynucleotide encoding said D-amino acid oxidase;
   b) a polynucleotide encoding said L-amino acid dehydrogenase; and
   c) a polynucleotide encoding said enzyme that regenerates NADH.

3. The method of either claim 1, wherein, in comparison to the starting organism, said recombinant microorganism has a higher concentration of *E. coli* catalase.

4. The method of either claim 1, wherein said recombinant microorganism is from a genus selected from the group consisting of: *Bacillus; Staphylococcus; Streptomyces;* and *Escherichia.*

5. The method of either claim 1, wherein said recombinant microorganism is of the species *Escherichia coli.*

6. The method of claim 1, wherein the cell wall of said recombinant microorganism is permeabilized by chemical or physical measures to allow for the absorption of a D-amino acid from the solution.

7. The method of either claim 1, wherein said D-amino acid is selected from the group consisting of: lysine, arginine, phenylalanine, valine, ornithine, leucine, histidine, norleucine, tyrosine, alanine, glutamate, and methionine.

8. The method of claim 1, wherein L-malate or L-malic acid is present when the polynucleotide encoding malate dehydrogenase is overexpressed.

9. The method of claim 1, wherein:
   a) said D-amino acid oxidase is selected from the group consisting of: the D-amino acid oxidase of *A. protophormiae;* the D-amino acid oxidase of *Trigonopsis variabilis;* the D-aspartate oxidase of *Bos taurus;* the D-amino acid oxidase of *Rhodosporidium;* and the D-amino acid oxidase of *Rhototorula gracillis;*
   b) said L-amino acid dehydrogenase is selected from the group consisting of: the L-leucine dehydrogenase of *Bacillus cereus;* the L-phenylalanine dehydrogenase of *Rhodococcus;* the L-lysine dehydrogenase of *Home sapiens;* the L-alanine dehydrogenase of *Bacillus subtilis;* and the glutamate dehydrogenase of *Bos taurus;*
   c) said polynucleotide encoding an enzyme that regenerates NADH is selected from the group consisting of: a formate dehydrogenase; a malate dehydrogenase; and an alcohol dehydrogenase, each from *A. protophormiae, T. variabilis* and *E. coli.*

10. The method of claim 9, wherein, in comparison to the starting organism said recombinant microorganism has a higher concentration of *E. coli* catalase.

11. The recombinant organism of claim 9, wherein said recombinant microorganism is from a genus selected from the group consisting of: *Bacillus; Staphylococcus; Streptomyces;* and *Escherichia.*

12. The recombinant microorganism of claim 9, wherein said recombinant microorganism is of the species *Escherichia coli.*

13. The method of claim 9, wherein the cell wall of said recombinant microorganism is permeabilized by chemical or physical measures to allow for the absorption of a D-amino acid from the solution.

14. The method of claims 9, wherein said D-amino acid is selected from the group consisting of: lysine, arginine, phenylalanine, valine, ornithine, leucine, histidine, norleucine, tyrosine, alanine, glutamate, cephalosporine, and methionine.

15. The method of claim 1, wherein L-malate or L-malic acid is present when the polynucleotide encoding malate dehydrogenase is overexpressed.

* * * * *